United States Patent
Dämmig et al.

(10) Patent No.: US 6,983,516 B2
(45) Date of Patent: Jan. 10, 2006

(54) SPINNING PREPARATION MACHINE

(75) Inventors: Joachim Dämmig, Ingolstadt (DE); Michael Ueding, Ingolstadt (DE); Chokri Cherif, Ingolstadt (DE)

(73) Assignee: Rieter Ingolstadt Spinnereimaschinenbau AG, Ingolstadt (DE)

( * ) Notice: Subject to any disclaimer, the term of this patent is extended or adjusted under 35 U.S.C. 154(b) by 66 days.

(21) Appl. No.: 10/406,576

(22) Filed: Apr. 3, 2003

(65) Prior Publication Data
US 2004/0194257 A1 Oct. 7, 2004

(30) Foreign Application Priority Data
Apr. 4, 2002 (DE) .......................... 102 14 955

(51) Int. Cl.
*D01H 5/32* (2006.01)

(52) U.S. Cl. ........................... 19/239; 19/150
(58) Field of Classification Search ................ 19/236, 19/238, 239, 65 A, 150, 157; 73/73, 865, 73/868; 57/264, 265; 324/633, 634, 636, 324/637, 640
See application file for complete search history.

(56) References Cited

U.S. PATENT DOCUMENTS

| | | | |
|---|---|---|---|
| 2,942,303 A | | 2/1960 | Bossen et al. |
| 4,887,155 A | | 12/1989 | Massen |
| 5,501,100 A | * | 3/1996 | Baechler et al. ............ 73/37.7 |
| 5,796,220 A | * | 8/1998 | Clapp et al. ................. 318/51 |
| 6,088,094 A | * | 7/2000 | Chu et al. ................. 356/238.3 |
| 6,119,312 A | * | 9/2000 | Leifeld ........................ 19/65 A |
| 6,286,188 B1 | * | 9/2001 | Muller et al. ................. 19/239 |
| 6,417,676 B1 | | 7/2002 | Schröder et al. |
| 6,476,619 B1 | * | 11/2002 | Moshe et al. ............... 324/634 |
| 2003/0150266 A1 | * | 8/2003 | Dammig et al. ............. 73/433 |

FOREIGN PATENT DOCUMENTS

| | | |
|---|---|---|
| DE | 4005548 A1 | 8/1991 |
| DE | 4034333 A1 | 12/1991 |
| DE | 4332347 A1 | 3/1995 |
| DE | 4445720 A1 | 6/1996 |
| EP | 0468023 B1 | 1/1992 |
| EP | 0468057 A1 | 1/1992 |
| WO | WO 0012974 A1 | 3/2000 |
| WO | WO 0055606 A2 | 9/2000 |

OTHER PUBLICATIONS

German Search Report, Aug. 16, 2002.

\* cited by examiner

*Primary Examiner*—Gary L. Welch
(74) *Attorney, Agent, or Firm*—Dority & Manning

(57) ABSTRACT

Different improvements of a spinning preparation machine are proposed to measure the fiber sliver thickness or the fiber sliver cross-section of at least one fiber sliver by means of one or several microwave sensors. One improvement is characterized by compressing means and special mechanical guiding elements that can be installed before, after and/or in the microwave sensor. It is also proposed to install a pair of conveyor rollers after a microwave sensor that can be designed in particular as an input roller pair of the subsequent drafting equipment. Furthermore, proposals are made for the calibration of the (at least one) microwave sensor.

58 Claims, 3 Drawing Sheets

SPINNING PREPARATION MACHINE

BACKGROUND OF THE INVENTION

The present invention relates to a spinning preparation machine as well as to a process for the calibration of a spinning preparation machine.

In the spinning industry, first a homogenized fiber sliver and finally, as an end product, a twisted yarn is produced in several process steps, e.g., from cotton. The spinning preparation machines upstream of the yarn production, such as cards, combing machines and drawing frames have in particular the task to even out the sliver mass fluctuations of one or several fiber slivers. For this purpose, sliver sensors are installed, e.g., on draw frames, and these measure the sliver thickness or sliver mass or their fluctuations, and transmit this information to an autoleveling unit that actuates at least one of the drafting elements of the drawing frame as required. One example of a draw frame operating according to such a regulating principle is model RSB-D30 of the RIETER Company. Even with drawing frame not equipped with autoleveling, information concerning the fluctuation of sliver thickness is desired in many instances. A suitable sensor at the output of such drawing frames emits a suitable switch-off signal for the machine and/or a warning signal, if a threshold value of the sliver mass or the sliver thickness is not reached or exceeded.

To measure the fluctuation of sliver thickness, mechanical scanning devices are known, and these are used today in almost all machines of this type. However, the dynamics of these mechanical sensors are no longer sufficient with output speeds of more than 1000 m/min and a high requirement profile. Furthermore, the strong mechanical compression that is necessary before the mechanical sensor has a negative effect on the drafting ability.

In addition to mechanical scanning of the fluctuation of sliver thickness, other scanning principles have been proposed. Thus, e.g., it is known from U.S. Pat. No. 2,942,303 and DE 44 45 720 A1 that the sliver thickness can be measured without contact, by means of penetrating optical radiation. The measuring precision is however strongly subject to environmental influences in that case, e.g., temperature, humidity and pollution.

Furthermore, the process is susceptible to color as well as to reflection characteristics of the fiber sliver.

With other known measuring techniques, contact-less measuring methods use ultrasound waves. Capacitive or pneumatic measuring methods are also known. It has also been proposed to use X-rays or gamma rays. However, all of these processes are sensitive to humidity. Therefore, it does not help much that climatic influences such as temperature and relative air humidity can be compensated for as a rule, so that climatic influences can be minimized. The problem of inherent fiber moisture cannot be easily removed thereby. In addition, the fiber moisture can vary by up to 5% in one and the same batch of cotton at constant environmental conditions. Also, the upper layers of cotton in a can presented to a spinning preparation machine absorb more moisture than the lower ones. Furthermore, the moisture of the textile fibers varies due to changes in climatic conditions in the spinning mill—e.g., moisture varies from the morning as compared to noon and night. The above-mentioned influences in turn exercise a great influence on the measuring results of sliver thickness, and thereby on the quality of regulating. Overall, these processes are therefore hardly suitable for high-precision measuring of the fiber sliver thickness.

A relatively new method to measure the sliver thickness is based on the utilization of microwaves. WO 00/12974 describes such a measuring system using microwaves, according to which microwaves were coupled to a resonator through which one or several fiber slivers are conveyed. The attenuation and the resonance frequency shift is then measured based on the presence of the fiber sliver or slivers, and the fluctuations of thickness and possibly the moisture content of the fiber sliver or slivers are derived from the measured values. EP 0 468 023 B1 describes a similar microwave measuring method that can be transferred to the measuring of fiber sliver. The sensors based on microwave resonator technology offer in particular the advantage that the environmental conditions, such as e.g. room temperature and room humidity, are already taken into account so that they need not be compensated for any further.

However, the sensors as well as the corresponding measuring methods described and shown in the above-mentioned publications are still underdeveloped in many aspects and in need of improvement. The specific adaptation to the problems of measuring fiber slivers in particular requires new solutions.

OBJECTS AND SUMMARY OF THE INVENTION

It is a principal object of the invention to improve the precision of measuring fiber slivers or a fiber structures by means of microwaves. Additional objects and advantages of the invention will be set forth in part in the following description, or may be obvious from the description, or may be learned through practice of the invention.

According to the first aspect of the invention, it is advantageous for precise measuring of the fiber sliver thickness for the fiber sliver material to be compressed, so that the distribution of material is as homogenous as possible in the measuring slit of the microwave sensor of which at least one is provided. The compressing means are preferably designed in form of mechanical guiding elements, e.g., in form of round rods against the round surfaces of which the fiber sliver material can glide, or in the form of an open or closed funnel. To realize such a compression, two variants are preferred, whereby the degree of compression can preferably be set or adjusted in function of the incoming sliver mass.

In one variant, the compression means are designed so that the compression means are installed directly before and/or after the sensor. The sensor can thus be mounted on the compression means or vice versa.

Alternatively, or in addition, at least one guiding element, preferably made of an electrically non-conductive material (e.g., ceramic), can be installed within the sensor. Preferably straight but also wedge-shaped or bow-shaped delimitations are possible.

It is advantageous if a targeted compression of the fiber sliver material leads to automatic cleaning effects of the measuring slit or of the resonator space.

As the material is introduced into the measuring slit, it must be ensured that the fiber slivers do not cross each other. For this purpose, for example, rakes, or sliver guide arrangements, can be installed before and/or after the sensor.

In an advantageous embodiment of the invention, a funnel is provided before the (at least one) sensor to compress or guide the fiber sliver(s). Following the (at least one) sensor, one or several rakes can be provided to prevent the fiber slivers from crossing each other.

According to a second aspect of the invention, a pair of draw-off rolls extending over the width of the fiber sliver is installed directly following the (at least one) microwave sensor preceding the draw frame. The longitudinal axes of the rolls extend at a right angle to the direction of fiber sliver movement. Therefore, the fiber sliver(s) can be drawn off from the sensor without being compressed substantially in their width.

A pair of draw-off rolls as input roller pair of the drawing frame following the sensor is especially preferred. This pair of draw-off rolls thus assumes the double function of drawing off the (at least one) fiber sliver as well as participation in the drafting.

In another aspect of the invention, the emphasis is on the cleaning of the sensor. Concerning the soiling of the microwave resonator, a distinction is to be made between two types of pollutants. On the one hand, they are easily removable pollutants such as, e.g., fiber fly, and, on the other hand, pollutants that are difficult to remove such as, e.g., honeydew and avivage. These two pollutants result in alterations of the characteristic values of the resonator, so that cleaning of the resonator(s) is proposed according to the invention.

The removal of pollutants can be carried out at regular intervals, preferably when the machine is stopped. The suitable cleaning apparatus to clean easily removable or resistant pollutants from the microwave resonator(s) can be triggered by suitable controls. In the alternative or in addition, the need for cleaning can be signaled when predefined limit values, e.g., with respect to characteristic resonator values in the empty state of the resonator are exceeded, or when the thickness of dirt or smeared pollutants is exceeded. Cleaning can be manual or by means of a cleaning apparatus or device. Manual cleaning may be absolutely necessary in some cases for the dirt that is difficult to remove.

The more easily removable dirt can be removed preferably by compressed air, whereby one or several air nozzles are directed upon the measuring slit of the resonator.

Control means are preferably available to cause the machine to stop in case of pollutants that are difficult to remove or cannot be removed. However, for reasons of productivity, cleaning of the easily removable as well as of the more resistant pollutants is carried out during can replacement at the draw frame outlet or during the replacement of feed cans, since the machine does not as a rule produce any fiber sliver at such time (except in case of a so-called flying exchange). The control means can be integrated into a central machine computer.

For the cleaning operation, the microwave sensor is designed preferably so as to be extensible, e.g., by means of a motor and a running rail on which the sensor can be moved, whereby the fiber sliver material's position remains preferably unchanged and is fixed in this position by suitably holding means. The sensor is preferably cleaned by means of compressed air or mechanical cleaning means that treat the resonator lining, e.g. ceramic, with care. On a stationary sensor, the dirt must be removed manually or automatically by means of compressed air, mechanical cleaning means, etc., from the measuring slit. After cleaning with, for example, compressed air, an electronic evaluation unit preferably can be used to evaluate the empty state (quality) of the characteristic resonator values, whether dirt still adheres or not, whereby the limit values for resistant material must be taken into account.

The controlling means for the control of sensor cleaning can be integrated into a central machine computer.

In order to minimize the degree of soiling of the resonator, the measuring space is preferably constructed so that an adhesion of impurities is reduced or even prevented. One possibility for this reduction/prevention consists of making the inner surface of the sensors in the form of dirt-repellent and abrasion proof materials and/or in avoiding sharp edges, especially at the input and output points of the fiber sliver material into the sensor.

A microwave sensor can be positioned at the input of the spinning preparation machine in various ways. On the one hand, an installation directly before the draw frame is possible. In this case, the pair of input rollers can be installed after the sensor and can be designed in such manner that the input roller pair of the draw frame is used to convey the material through the measuring slit of the sensor (see above). The distance between sensor and input roller pair is advantageously smaller than the median staple length so that uncontrolled fiber movements may be avoided during this conveying process.

In alternative or additional embodiments, a microwave sensor can be installed in the preliminary drafting field of the draw frame, constituted by the input and the central pairs of rolls, and/or in the main drafting field of the draw frame, constituted by central and delivery roller pairs.

In order to position a microwave sensor at the output of the spinning preparation machine, several possibilities exist. Thus, for example, a placement between a fleece nozzle downstream of the draw frame and a calendar roller pair further downstream is possible.

Designing the sensor in the form of fleece nozzle insert is also advantageous, whereby the sensor assumes in this case the function of a sliver former. With such a design, the sensor can be given a closed form, e.g., cylindrical in cross-section. Of course, other geometric forms are also possible, e.g., a design with elliptical or rectangular cross-section. A threading function is advantageously integrated into the fleece nozzle insert, e.g., in the form of air nozzles. Alternatively, the fleece nozzle can be integrated into the microwave sensor.

In another preferred embodiment, a microwave sensor is located directly after the output roller pair of the drafting equipment. In this case, the sensor can be open, e.g., in the form of a fork-shaped slit. The form of the sliver is then changed by a downstream fleece nozzle.

A microwave sensor can also be positioned between calendar roller pair and rotary plate.

The spinning preparation machine is preferably equipped with threading means to thread the fiber sliver material automatically into the (at least one) sensor as new batches are processed or when sliver breakage is being repaired. Such threading means may comprise, e.g., one or several air nozzles, so that the fiber sliver material is seized by the air stream produced and is introduced into the sensor. Alternatively or in addition, the threading means can also function mechanically, e.g., by clamping and moving or introducing the fiber sliver(s) into the measuring slit of the resonator.

In addition, the threading means may comprise mechanical holding means or holding devices, e.g., clamps, by means of which the fiber sliver material can be held in a defined position during cleaning operations (see above) after extension of the sensors from a measuring position into a cleaning position. In this manner, the material can then be introduced without manual intervention into the measuring slit of the sensor that is returned to its measuring position.

According to one aspect of the invention, it was realized that the fiber material might show different evolutions of temperature at the input and output of the draw frame, so that these could falsify the measuring results. It is therefore proposed according to the invention that the spinning preparation machine be provided with a device to continuously measure temperatures, so as to determine the temperatures of the textile fiber material, preferably with at least one temperature sensor (including start/stop phase and in particular cold start) and to thus compensate for the measuring results. According to an advantageous embodiment of the invention, this compensation can be realized in the electronic measuring system of the microwave sensor or through external compensation. In this manner in particular, cross-relationships of the measuring results at the input and output can be established, whereby preferably the different sliver speeds at the input and at the output as well as the running time between the two sensors are taken into account, e.g., in a central computer of the machine. Depending on the temperature difference between the material at the input and at the output, a correction should be made (offset correction).

When sensors are used that employ microwaves, the electrical conductivity of delustering elements and pigments in cotton to be drafted or that has been drafted, is in most cases insignificant. In case of electrically conductive materials, such as, e.g., carbon fiber, the same microwave sensor can possibly be used. Also, a second sensor, preferably based on different physical principles, can be used.

If at least two resonators are connected one after the other at a measuring position—i.e., either at the input or at the output—they preferably can be used to constitute a band filter.

According to another aspect of the invention, at least one microwave sensor is provided to measure the fiber sliver thickness at the input, and at least one microwave sensor to measure the fiber sliver thickness at the output, whereby the target sliver thickness of the fiber sliver leaving the machine can be preset, e.g., on a machine display. The machine is designed so that the actual sliver thickness measured by at least one sensor at the input and by at least one sensor at the output are integrated in a central machine by means of an evaluation unit, e.g., a central machine computer. These measurements can be correlated with each other and the results can be transmitted to a control unit in order to actuate the drafting elements in accordance with the preset target sliver thickness. The evaluation unit preferably is used to establish a cross-correlation between the actual sliver thickness measured by the (at least one) sensor at the input and the (at least one) sensor at the output. A subsequent plausibility control is advantageous.

To calibrate the (at least one) microwave sensor, calibration curves for different materials preferably are used, whereby these curves can be stored in the measuring electronics and/or whereby the curves can be called up from external electronic media, e.g., via the Internet, a compact disk, etc. as needed.

For every type of fiber material, e.g., cotton, polyester, viscose, polyacrylic nitrile, etc., at least one calibration curve preferably is established. Several calibration curves can also be adopted advantageously as functions of the degree of curling, moisture absorption capacity, level of pretreatment, level of pollution, etc.

When fiber mixtures are involved, e.g., flock or sliver mixtures, new calibration curves must be determined as a function of the mixture ratio. These curves can be stored, e.g., in an electronic memory or, based on an input of the mixture ratio, can be calculated or determined from the corresponding individual calibration curves. For these mathematical operations, e.g., mean calculations, interpolations or regressions are used in particular. Alternatively or in addition, the data for mixture ratios are stored in an electronic memory or can be written into such a memory based on the above calculations. In this manner, a data bank of the different mixture combinations is available to the user, and the user can poll the data bank for the batch currently to be drafted.

To enter the mixture ratios, the spinning preparation machine is advantageously equipped with a suitably designed input unit as well as with a processing unit to determine the calibration curves based on the entered mixture ratios.

Textile fiber slivers in skein form with defined moisture contents preferably are used as the calibration means. For this determination, conditioned samples are available, in which the fiber moisture is known precisely. Alternatively, the entire fiber material is stored under the same environmental conditions. Here, part of this fiber material is used as calibration means. It is also possible to combine these two methods.

Alternatively, the material to be drafted is weighed under normal production conditions in a defined length, is then dried and weighed again. The moisture is determined by comparing this sliver thickness. The sliver thickness and the calculated moisture content are then put at the disposal of the evaluation unit. It is also possible to process sliver masses instead of sliver thickness. The calibration curve is determined from the weighed sliver thickness and the appertaining characteristic resonator values, i.e., frequency shift A and moisture content $\phi$. The essentially linear function "frequency shift protracted against sliver thickness", generally going through the zero point, is in this case measured under normal production conditions by means of the microwave sensor and is associated with the fiber moisture calculated from weighing. Advantageously, at least one second measuring point of the same material with different moisture content is determined. Thereby, different moisture contents can be determined in course of production.

In a continued calibration, the microwave output sensor is post-calibrated on the basis of laboratory measurements where, e.g., the actual sliver thickness (and/or the sliver moisture) of the drafted fiber sliver is measured (plausibility control). Based on this post-calibration, i.e., on the current characteristic line of the output sensor, the microwave input sensor is post-calibrated advantageously while especially taking into account the different fiber sliver temperatures at the input and output and other influences, e.g., soiling of the sensor. This can be advantageous, for example, when the entering and exiting fiber sliver material has different temperatures that influence the measuring results. The post-calibration is effected preferably automatically, by means of a microprocessor.

For rapid calibration of the microwave sensors, defined textile samples in polymer combinations are preferably poured in with known masses. Alternatively, output polymers of the fiber materials (filament yarns) concerned are used, e.g., melted viscose masses. The samples have preferably different, known moisture contents.

Samples with a relative permittivity nearly identical with that of the fiber sliver material to be processed are advantageously used for the calibration of the (at least one) microwave sensor.

Preferably, one single evaluation electronic system is used for all the resonators at the draw frame input and/or draw frame output.

The invention in its different aspects can be used with cards, draw frames as well as combing machines, with autoleveling as well as non-autoleveling drawing equipment. An application of the invention in a combination of card and downstream draw frame is also advantageous.

The invention is explained below in its different aspects through the figures.

DETAILED DESCRIPTION

Reference will now be made in detail to the presently preferred embodiments of the invention, one or more examples of which are shown in the figures. Each example is provided to explain the invention, and not as a limitation of the invention. In fact, features illustrated or described as part of one embodiment can be used with another embodiment to yield still a further embodiment. It is intended that the present invention cover such modification and variations.

Figure 1:
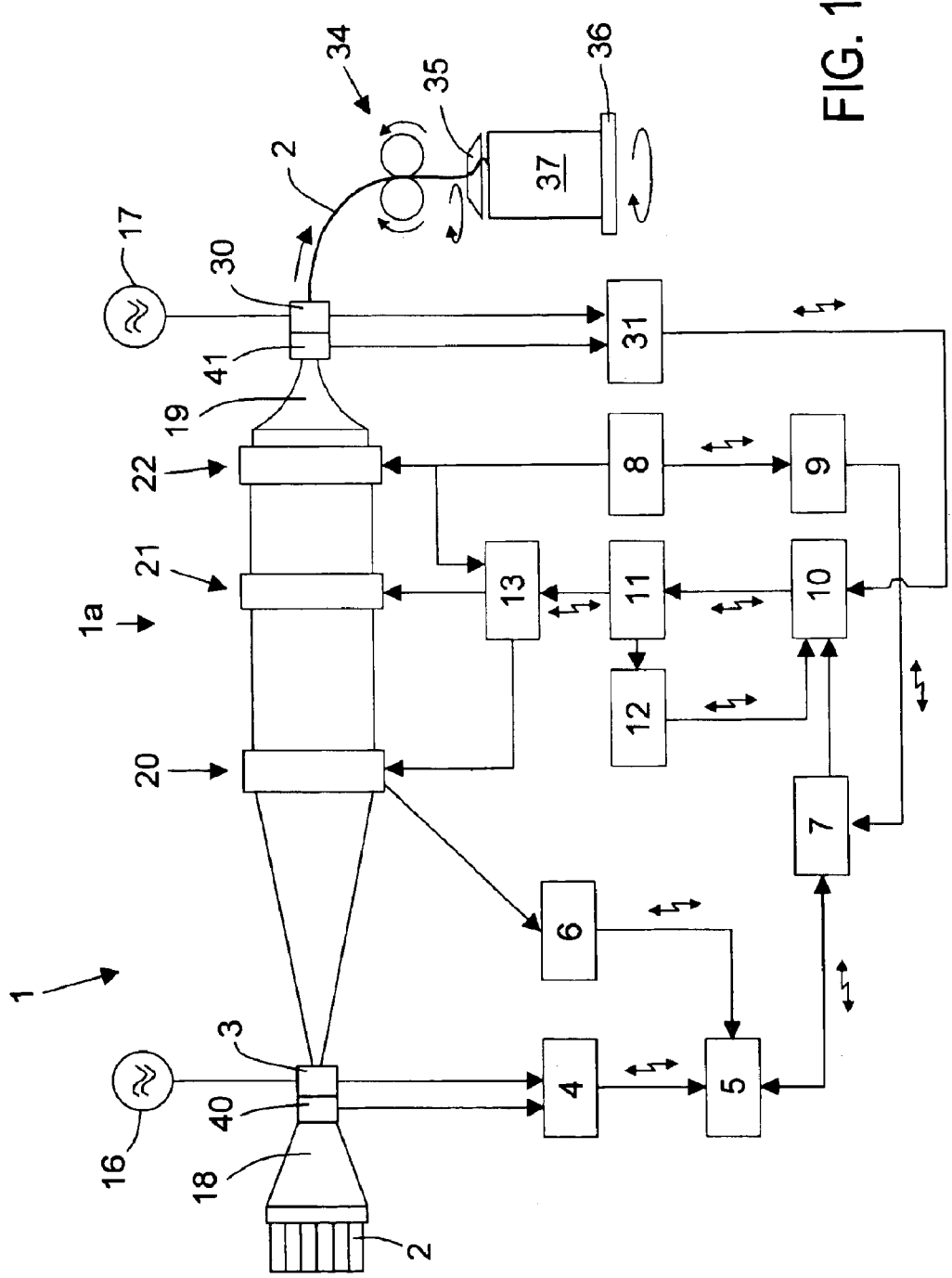
FIG. 1 schematically shows an autoleveling draw frame with autoleveling components.

FIG. 1 is a schematic example of an autoleveling principle on a draw frame 1. At the input of the draw frame 1, the sliver thickness of entering fiber slivers 2—in this case six fiber slivers 2—is detected by a microwave sensor 3 functioning on the resonator principle. The microwave sensor 3 is connected to a microwave generator 16 that is actuated by a processor unit (not shown) and introduces microwaves into the resonator of the microwave sensor 3. A funnel 18, serving as a compressing means, is installed upstream of the microwave sensor 3 to compress the fiber slivers 2. When they have passed the microwave sensor 3, the fiber slivers 2 are again spread out in order to enter the draw frame 1a. The measured values of the microwave sensor 3 are converted by an evaluation unit 4 into voltage values representing the sliver thickness fluctuations and these are conveyed to a memory 5 (electrical signals are represented by a double lightning arrow in FIG. 1, while mechanical signals are not given any special marking). The memory 5 transmits the measurement voltage by means of an impulse generator or clock generator 6 with defined time delay to a target value phase 7. The clock generator 6 receives a triggering signal (a so-called "redefined constant scanning length") from an input roller pair 20 serving at the same time to convey the fiber slivers 2 through the microwave sensor 3. Alternatively, the impulse generator can be coupled to another pair of rollers, e.g., with a conveying roller pair (not shown) directly after the microwave sensor 3 (as seen in the direction of sliver movement). In such case, it is not the input roller pair 20 that is used to convey the fiber slivers 2 through the sensor microwave sensor 3, but the conveyor roller pair.

The target value phase 7 furthermore receives a guide voltage from a conducting tachometer 9 that is a measure for the rotational speed of the lower roller of a delivery roller pair 22 driven by a main motor 8. Following this, a target voltage is calculated in the target value phase 7 and is transmitted to a control unit 10. In the control unit 10, a comparison is made between target value and actual value and is used to impart a specific rotational speed to a variable speed motor 11 that corresponds to the desired change in drafting. In this process, the target values of the variable speed motor 11 are transmitted to an actual-value tachometer 12, which then retransmits the corresponding actual voltage to the control unit 10. The variable speed motor 11 drives in a planetary gear 13 driven by the main motor 8, whereby the planetary gear 13 modifies the rotational speeds of the lower roller of the input roller pair 20 and of a lower roller of a central roller pair 21 so that a homogenization of the drafting of the sliver takes place.

The sliver thickness serves as the magnitude for leveling. Based on the movement of the fiber sliver from the microwave sensor 3 to the drafting field consisting of input, central and delivery roller pairs 20, 21, 22 (the roller pairs are shown in the top view), a dead time is calculated. The rotational speed of the variable speed motor 11 as an actuating magnitude is determined by the control unit 10, wherein the actual thickness of the fiber slivers 2, the target value sliver thickness as guiding magnitude, and the rotational speeds of the main motor 8 and the variable speed motor 11 are processed. Due to the proportional superimposition of the rotational speeds of the main motor 8 and of the variable speed motor 11, and taking into account the mentioned dead time, the sliver thickness is leveled in the drafting equipment 1a in the so-called leveling application point.

At the output of the drafting equipment 1a, a resonator of a microwave sensor 30 connected to an additional microwave generator 17 is installed and is connected downstream of the sliver funnel or fleece nozzle 19 shown in the example of the embodiment in the form of a compressing means. The signals of the microwave sensor 30 are transmitted to an evaluation unit 31 that emits electrical voltage signals corresponding to the sliver thickness of the drafted fiber sliver 2 and transmits them to the control unit 10. Alternatively or in addition, the results of the microwave sensor 30 serve merely to monitor the sliver and for sliver quality control. Accordingly, these results are preferably displayed on the machine and/or on a central unit in the spinning plant.

Different circuit arrangements are possible in particular the utilization of a central computer.

The drafted fiber sliver 2 is drawn from the microwave sensor 30 by means of calendar rollers 34 (the distances between microwave sensor 30 and rollers 34 are not to scale) and are deposited by means of a sliver channel located in a rotating rotary plate 35 in a round can 37 standing on a rotating can plate 36. Alternatively, the can plate 36 is in form of a flat can traversing back and forth.

At the drafting equipment input and at the drafting equipment output, apparatuses 40 and 41, respectively, are installed for the preferably continuous measuring of the fiber sliver temperature (in FIG. 1 in immediate proximity of the corresponding sensor 3 or 30). The measured temperature values or the voltage values characterizing the temperature are transmitted to the corresponding evaluation unit 4 or 31 which assumes here in addition the function of a compensation unit for temperature compensation of the measured results supplied of the sensors 3 or 30. The results of the evaluation unit 4 or 31 can be correlated, e.g., by means of cross-correlation. Such a correlation can be effected, e.g., in the control unit 10 which must be able to perform the computations necessary for that purpose. Alternatively, separate processor units or one common processor unit can be provided for temperature compensation and, if necessary, also for correlation of the signals coming from the apparatuses 40 and 41.

The two sensors 3, 30 can preferably be cleaned automatically, e.g., by compressed air coming from one or several air nozzles directed on the measuring slit of the corresponding sensor 3, 30. Corresponding controls (not shown) trigger such cleaning, preferably at timely intervals and/or when a limit value of the quality of the characteristic resonator values is exceeded and/or when predetermined thicknesses of dirt or smudging film is exceeded. Such air nozzles can also serve as threading means for the automatic threading of the fiber sliver(s) to be measured in the (at least one) sensor 3 or 30.

In an alternative embodiment of the invention that is not shown, the spinning preparation machine can be provided with individual drives, each of which preferably with its own control circuits, whereby a central computer is advantageously used.

Figure 2:
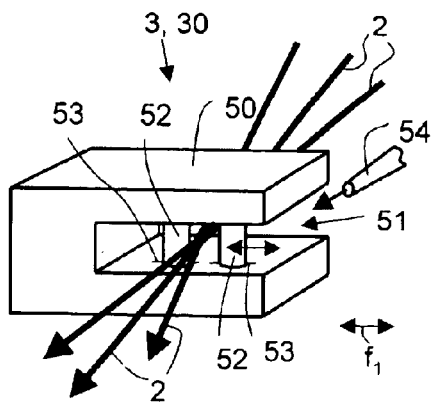
FIG. 2 shows an open microwave sensor in perspective.

FIG. 2 shows an open microwave sensor 3, 30 consisting of a resonator 50 bent into a U-shape in which the opening is a measuring slit 51 through which one or several fiber slivers 2, indicated schematically as arrows, can be conveyed. In the measuring slit 51, on either side of the fiber sliver(s) 2, a round rod 52 is provided, whereby the two round rods 52 together serve as compressing guide elements. The round rods 52 can be displaced on schematically indicated guides 53 at a right angle to the sliver (see double arrow) and can preferably be fixed in their position. In order to introduce the fiber sliver(s) 2 into the measuring slit 51 and between the two round rods 52, one or several air nozzles 54 are provided and are directed essentially in the direction of sliver movement (in FIG. 2, they move towards the viewer) and carry the fiber sliver along thanks to the compressed air (see arrow). Furthermore, the double arrow f1 indicates that the entire sensor 3, 30 can be moved from a measuring position into a cleaning position and back into the measuring position.

FIGS. 3–6 show to further embodiments of a microwave sensor 3 located at the input of the drafting equipment. In the top view of FIG. 2, an input table can be seen at whose end towards the presentation cans (not shown) a sliver guide, or a rake, arrangement 24 is provided. The sliver guide, or rake, arrangement 24 consists of nine vertically positioned round rods between which eight fiber slivers 2 are taken from the presentation cans to the microwave sensor 3 (the fiber slivers 2 are indicated by dots in the side view of FIG. 4 when they run under cover). Following the rake arrangement 24 are two parallel driven conveyor rollers 25 on which four jockey or load rollers 26 aligned with each other are placed. Two of the eight slivers 2 run between each of the jockey rollers 26 and the conveyor rollers 25 beneath it. In case of sliver breakage, an electrical contact is established between the jockey rollers 26 concerned. The jockey rollers 26 and the breakage then is displayed in a manner recognizable to an operator.

A horizontally oriented round rod 27 that may be immobile or rotatable and over which the fiber slivers 2 are conveyed follows in the direction of sliver movement. Furthermore, the vertical double arrow in FIG. 4 indicates that the round rod 27 can be preferably adjusted vertically. Following the round rod 27 are two vertical guiding elements 28 having a circular cross-section, between which the fiber slivers 2 run. The distance between the two guiding elements 28 is preferably adjustable as is indicated by the corresponding double arrows in FIG. 3.

Figure 4:
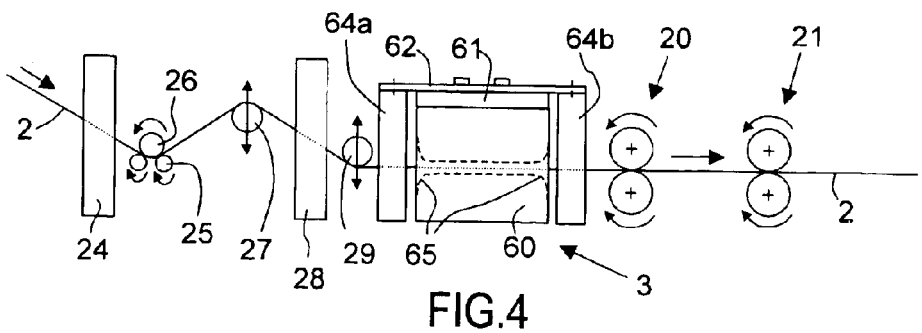
FIG. 4 shows a lateral view of the draw frame input of FIG. 3.

The guiding elements 28 are followed in the direction of sliver movement by a second round rod 29 extending horizontally, which can also be supported so as to be immobile or rotatable, and beneath which the fiber slivers 2 are conveyed. The second round rod 29 which, according to FIG. 4, is vertically adjustable (see double arrow) serves for the centered introduction of the fiber slivers 2 into the resonator 60 of the microwave sensor 3. Another two vertical guiding elements 64a with round cross-section are provided between the round rod 29 and the microwave sensor 3. These are attached at the top to flat rods 62 extending horizontally in the direction of fiber movement that are in turn attached by means of screws located in two corresponding elongated holes 63 to a cover plate 61. The cover plate 61 is mounted on the resonator 60. At the sliver output side of the sensor 3, guiding elements 64b attached in the same manner are provided. The distance between the guiding elements 64a, 64b can be adjusted by displacing the flat rods 62 in the elongated holes 63.

Figure 3:
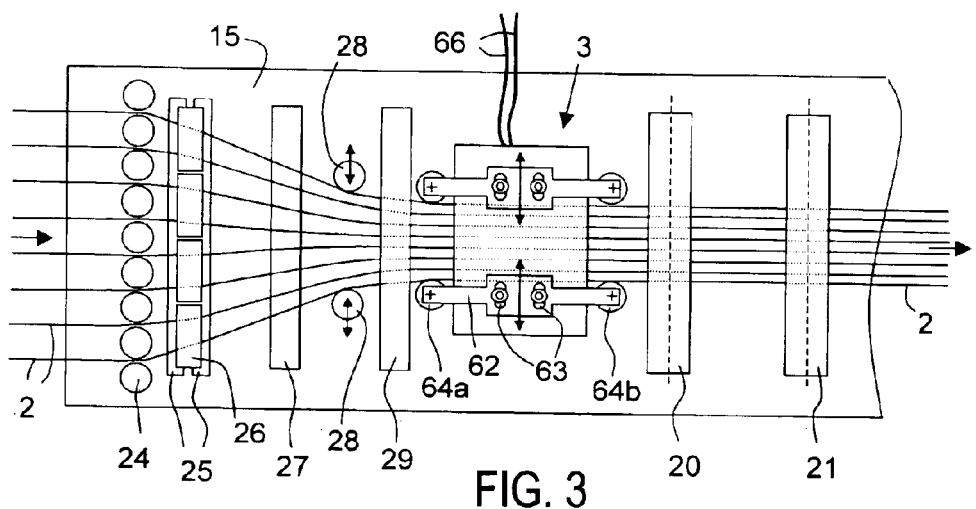
FIG. 3 shows a top view of the input of a draw frame with a closed microwave sensor.

At the input and at the output of the sensor 3 whose connection cables 66 (to a microwave generator and to a signal receiver) are also shown in FIG. 3, horizontally extending rounded edges 65 that extend along the fiber sliver width are provided as additional guiding elements (see FIG. 4, represented by broken lines). These guiding elements 65 are thus located in the sensor 3 and are used for steady guidance of the fiber slivers 2 through the resonator 60.

An input roller pair 20 that draws the fiber slivers 2 from the sensor 3 is installed downstream of the guiding elements 64b. This roller pair is advantageously designed as an input roller pair 20 of the downstream drafting equipment 1a (see FIG. 1). Contrary to the mechanical measuring devices that compress the fiber slivers 2 and after which the fiber slivers 2 must be spread out again before entering the drafting equipment 1a, the space consumed by spreading out the fiber slivers 2 can be dispensed with. The entire machine can thus be much more compact. The input roller pair 20 serves on the one hand to draw the slivers 2 from the sensor 3 and on the other hand as a drafting element. The fiber slivers 2 run essentially parallel to each other through the sensor and continue into the drafting equipment 1a.

The guiding elements 28, 64a and 64b for the lateral guidance of the fiber slivers 2 can be provided alternatively or in addition to their linear adjustability in the direction at a right angle to the slivers (see FIG. 3) with an eccentric cross-section avoiding sharp circumferential edges (not shown). In order to change the passage width of the fiber slivers 2, these guiding elements 28, 64a, 64b can be rotated around their longitudinal axis and can be stopped in their position.

Figure 5:
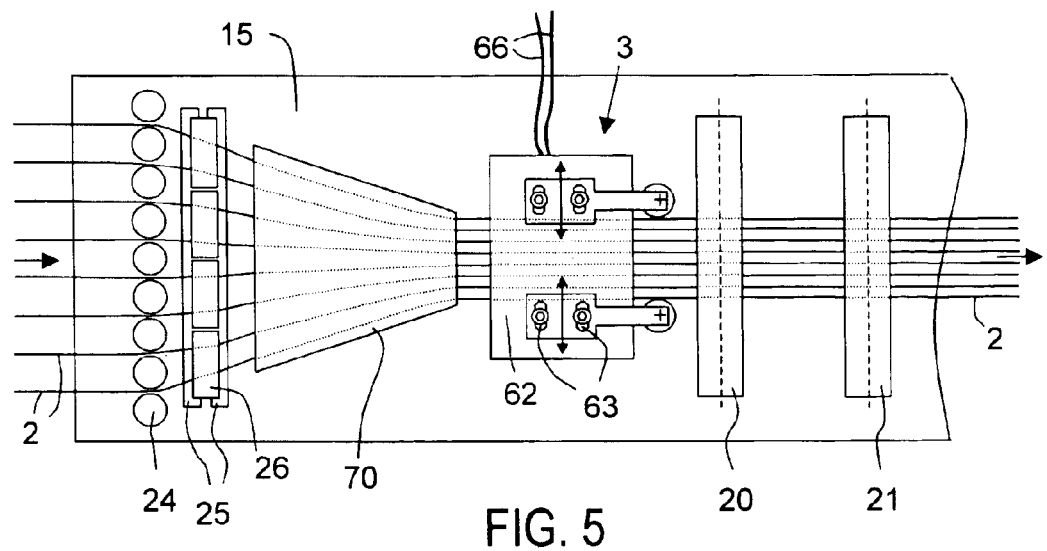
FIG. 5 shows a top view of the input of a draw frame with a closed microwave sensor according to a second embodiment.
Figure 6:
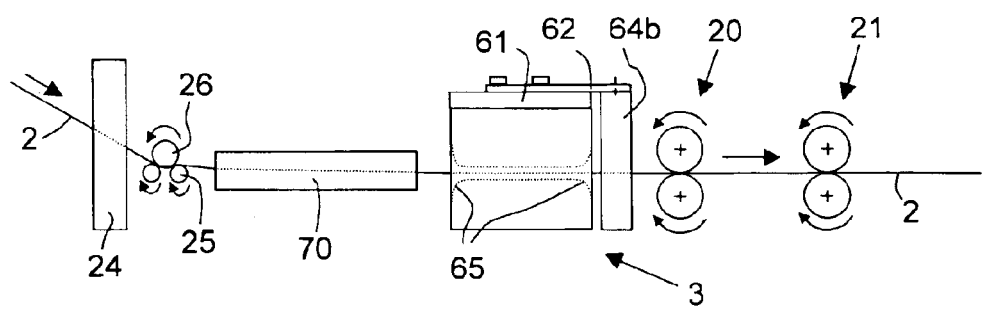
FIG. 6 shows a lateral view of the embodiment of FIG. 5.

According to the embodiments shown in the FIGS. 5 and 6, a funnel 70 is provided before the sensor 3, through which the fiber slivers 2 are guided following the jockey and conveying rollers 26, 25. Preferably, the input and/or output width of the funnel 70 can be advantageously adjusted. The embodiment shown in FIGS. 5 and 6 is otherwise identical to those of FIGS. 3 and 4. It should be mentioned that the guiding elements 64b at the output of the sensor 3 are superfluous because of the funnel 70. If, however, the output width of the funnel 70 is not adjustable, the presence of guiding elements 64a can be advantageous.

The (at least one) sensor (3, 30) can be calibrated on the basis of calibration curves for different fiber sliver materials and/or fiber sliver mixtures. The calibration curves can be stored in the electronic measuring system (i.e., evaluation unit 4 or control unit 10) and/or can be called up from an external media 100 (i.e., internet, computer, compact disk, etc.) when needed. For different fiber sliver materials, at least one calibration curve can be provided and called up for each fiber sliver material; it being possible to switch over among the different calibration curves. A new calibration curve can be determined on the basis of predetermined mixture ratios in case of fiber sliver mixtures. The new calibration curve can be accomplished by taking the mean, interpolation and/or regression of at least two calibration curves.

Data, preferably in the form of tables pertaining to the calibration curves of different fiber sliver materials, can be stored in an electronic memory 4, 10, 31, 100 to determine new calibration curves. The spinning preparation machine can have an input unit 100 for the input of the mixture ratios as well as by a processor unit 4, 31 to determine a calibration curve from the entered mixture ratios.

A microwave sensor (3) can be post-calibrated at the drafting equipment input by a post-calibrated microwave sensor (30) at the drafting equipment output by means of a microprocessors 4, 31, 10.

A process also exists for the calibration of a spinning preparation machine. A microwave output sensor (30) is post-calibrated based on laboratory measurements in which, e.g., the actual sliver thickness of the drafted fiber sliver is measured (plausibility control). Subsequently, a microwave input sensor (3) is post-calibrated automatically or manually based on this post-calibration. In the laboratory, skeins of fiber slivers with defined moisture content are used for calibration. In the alternative, the entire fiber sliver is stored under uniform environmental conditions and part of this fiber sliver material is used for calibration.

For rapid calibration for polymers (to be made into fibers), textile calibration samples are poured into hardening materials, e.g., polymers. Alternatively, in that output polymers of the corresponding fiber materials, e.g., melted viscose, are used. Textile calibration samples of material with the same relative permittivity as the fiber sliver material to be processed are advantageously used for the calibration of the microwave sensor 3, 30.

It will be appreciated by those skilled in the art that various modifications and variations can e made in the present invention without departing from the scope of the invention. It is intended that the present invention include such modifications and variations as come within the scope of the appended claims and their equivalents.

What is claimed is:

1. A spinning preparation machine with autoleveling drafting equipment for drafting at least one fiber sliver, said spinning preparation machine including:
    a microwave sensor through which said fiber sliver passes to measure fiber sliver thickness, said microwave sensor carried within said spinning preparation machine proximal to at least one of an input of said drafting equipment or an output of said drafting equipment; and
    a compressing element positioned proximal to said microwave sensor, said compressing element compressing said fiber sliver to obtain a homogenous distribution of said fiber sliver passing through said microwave sensor.
2. A spinning preparation machine as in claim 1, wherein said compressing element is a mechanical guide.
3. A spinning preparation machine as in claim 2, wherein said mechanical guide is disposed within said microwave sensor.
4. A spinning preparation machine as in claim 3, wherein said mechanical guide has horizontal rounded edges which are rounded in the direction of fiber sliver movement at least at the input of said microwave sensor.
5. A spinning preparation machine as in claim 2, wherein said mechanical guide includes an electrically non-conductive material.
6. A spinning preparation machine as in claim 5, wherein said electrically non-conductive material is ceramic.
7. A spinning preparation machine as in claim 2, wherein said mechanical guide is positioned directly before said microwave sensor.
8. A spinning preparation machine as in claim 2, wherein said mechanical guide is positioned directly after said microwave sensor.
9. A spinning preparation machine as in claim 2, wherein said mechanical guide is positioned directly before and after said microwave sensor.
10. A spinning preparation machine as in claim 2, wherein said mechanical guide is adjustable to change the passage width for said fiber sliver.
11. A spinning preparation machine as in claim 1, further including a sliver guide arrangement positioned before said microwave sensor.
12. A spinning preparation machine as in claim 1, further including a sliver guide arrangement positioned after said microwave sensor.
13. A spinning preparation machine as in claim 1, further including a roller pair of said drafting equipment disposed within said spinning preparation machine downstream in the direction of said fiber sliver movement from said microwave sensor.
14. A spinning preparation machine as in claim 13, wherein said roller pair is an input roller pair of said drafting equipment.
15. A spinning preparation machine as in claim 14, wherein said microwave sensor is located in a preliminary drafting field of said drafting equipment proximal to said input roller pair.
16. A spinning preparation machine as in claim 15, wherein said input roller pair conveys said fiber sliver through said microwave sensor.
17. A spinning preparation machine as in claim 16, wherein the distance between said microwave sensor and said input roller pair is less than the median staple length of fibers within said fiber sliver being drafted.
18. A spinning preparation machine as in claim 1, wherein said microwave sensor is located in a main drafting field of the drafting equipment.
19. A spinning preparation machine as in claim 1, further including a compressed air nozzle positioned before said microwave sensor in the direction of said fiber sliver movement directing air through said microwave sensor.
20. A spinning preparation machine as in claim 1, further including an evaluation unit in communication with said microwave sensor, said evaluation unit receiving measured results from said connected microwave sensor.
21. A spinning preparation machine as in claim 20, comprising a first microwave sensor before said input of said drafting equipment and a second microwave sensor after said output of said drafting equipment, and said evaluation unit connected to each of said microwave sensors whereby said evaluation unit sends measured results from said first and second microwave sensors to a control unit to correlate such measured results.
22. A spinning preparation machine with autoleveling drafting equipment for drafting at least one fiber sliver, said spinning preparation machine including:
    a microwave sensor for measuring fiber sliver thickness, said microwave sensor carried within said spinning preparation machine proximal to at least one of an input of said drafting equipment or an output of said drafting equipment;

said microwave sensor including a resonator through which said fiber sliver passes, said resonator generating characteristic resonator values to aid said microwave sensor in measuring said fiber sliver thickness; and a cleaning device carried within said spinning preparation machine and proximal to said microwave sensor, said cleaning device cleaning said microwave sensor, including said resonator, upon occurrence of at least one of regular intervals, a limit value of characteristic resonator values being exceeded or a predetermined film thickness of dirt or smudging that accumulates on said resonator being exceeded.

23. A spinning preparation machine as in claim 22, further including a control unit carried within said spinning preparation machine and in communication with said microwave sensor and said cleaning device.

24. A spinning preparation machine as in claim 22, wherein said cleaning device is a compressed air nozzle.

25. A spinning preparation machine as in claim 22, further including an evaluation unit carried within said spinning preparation machine and in communication with said microwave sensor and said cleaning device, said evaluation unit evaluating the characteristic resonator values when said resonator is in an empty state either before or after a cleaning of said sensor to determine a degree of pollution on said resonator.

26. A spinning preparation machine as in claim 25, wherein said evaluation unit evaluates the characteristic resonator values when said resonator is in an empty state both before and after a cleaning of said sensor to determine the degree of pollution on said resonator.

27. A spinning preparation machine with autoleveling drafting equipment for drafting at least one fiber sliver, said spinning preparation machine including:

a microwave sensor for measuring fiber sliver thickness, said microwave sensor carried within said spinning preparation machine proximal to at least one of an input of said drafting equipment or an output of said drafting equipment;

said microwave sensor including a resonator through which said fiber sliver passes, said resonator generating characteristic resonator values to aid said microwave sensor in measuring said fiber sliver thickness;

a cleaning device carried within said spinning preparation machine and proximal to said microwave sensor, said cleaning device cleaning said microwave sensor at regular intervals;

a control unit carried within said spinning preparation machine and in communication with said microwave sensor and said cleaning device; and wherein said control unit switches off the machine when said characteristic resonator values exceed limit values designating degrees of pollution.

28. A spinning preparation machine with autoleveling drafting equipment for drafting at least one fiber sliver, said spinning preparation machine including:

a microwave sensor for measuring fiber sliver thickness, said microwave sensor carried within said spinning preparation machine proximal to at least one of an input of said drafting equipment or an output of said drafting equipment;

said microwave sensor including a resonator through which said fiber sliver passes, said resonator generating characteristic resonator values to aid said microwave sensor in measuring said fiber sliver thickness;

a cleaning device carried within said spinning preparation machine and proximal to said microwave sensor, said cleaning device cleaning said microwave sensor at regular intervals;

a control unit carried within said spinning preparation machine and in communication with said microwave sensor and said cleaning device; and wherein said control unit activates said cleaning device when cans that collect drafted fiber sliver exiting said drafting equipment are replaced.

29. A spinning preparation machine with autoleveling drafting equipment for drafting at least one fiber sliver, said spinning preparation machine including:

an input roller pair being an initial roller pair for said drafting equipment through which said fiber sliver passes;

an output roller pair located downstream in the direction of said fiber sliver movement from said input roller pair, said output roller pair being the last roller pair of said drafting equipment;

a fleece nozzle located downstream in the direction of said fiber sliver movement from said output roller pair, said fleece nozzle compressing said drafted fiber sliver as said drafted fiber sliver exits said drafting equipment;

a calendar roller pair located downstream in the direction of said fiber sliver movement from said fleece nozzle, said calendar roller pair further compressing and transporting said drafted fiber sliver;

a rotary plate located downstream in the direction of said fiber sliver movement from said calendar roller pair, said rotary plate having a sliver channel which receives said drafted fiber sliver from said calendar roller pair and deposits said drafted fiber sliver into a can; and a microwave sensor through which said fiber sliver passes to measure fiber sliver thickness, said microwave sensor carried within said spinning preparation machine proximal to at least one of said fleece nozzle or said calendar roller pair.

30. A spinning preparation machine as in claim 29, wherein said microwave sensor is configured as a component of said fleece nozzle.

31. A spinning preparation machine as in claim 29, wherein said fleece nozzle is integrated into said microwave sensor.

32. A spinning preparation machine as in claim 29, wherein said microwave sensor is located between said output roller pair and said fleece nozzle.

33. A spinning preparation machine as in claim 29, wherein said microwave sensor is located between said fleece nozzle and said calendar roller pair.

34. A spinning preparation machine as in claim 29, wherein said microwave sensor is located between said calendar roller pair and said rotary plate.

35. A spinning preparation machine as in claim 29, further including a compressed air nozzle positioned before said microwave sensor directing air through said microwave sensor.

36. A spinning preparation machine with autoleveling drafting equipment for drafting at least one fiber sliver, said spinning preparation machine including:

a microwave sensor for measuring fiber sliver thickness, said microwave sensor carried within said spinning preparation machine proximal to at least one of an input of said drafting equipment or an output of said drafting equipment;

said microwave sensor including a resonator through which said fiber sliver passes, said resonator generating characteristic resonator values to aid said microwave sensor in measuring said fiber sliver thickness; and a threading device positioned proximal to said microwave sensor, said threading device threading said fiber sliver through said resonator of said microwave sensor.

37. A spinning preparation machine as in claim 36, wherein said threading device comprises a compressed air nozzle.

38. A spinning preparation machine with autoleveling drafting equipment for drafting at least one fiber sliver, said spinning preparation machine including:

a microwave sensor for measuring fiber sliver thickness, said microwave sensor carried within said spinning preparation machine proximal to at least one of an input of said drafting equipment and an output of said drafting equipment;

said microwave sensor including a resonator through which said fiber sliver passes, said resonator generating characteristic resonator values to aid said microwave sensor in measuring said fiber sliver thickness; and a threading device positioned proximal to said microwave sensor, said threading device threading said fiber sliver through said resonator of said microwave sensor; and wherein said threading device comprises a clamp which holds said fiber sliver in a defined position as said microwave sensor is moved from a measuring position to a cleaning position and back to said measuring position, permitting reintroduction of said fiber sliver without manual intervention.

39. A spinning preparation machine with autoleveling drafting equipment for drafting at least one fiber sliver, said spinning preparation machine including:

a microwave sensor through which said fiber sliver passes to measure fiber sliver thickness, said microwave sensor carried within said spinning preparation machine proximal to at least one of an input of said drafting equipment or an output of said drafting equipment;

a temperature apparatus disposed proximal to said microwave sensor, said temperature apparatus measuring the temperature of said fiber sliver as said fiber sliver passes said temperature apparatus; and a compensation unit connected to said microwave sensor and said temperature apparatus, said compensation unit processing measured temperatures received from said temperature apparatus and providing compensation values to said microwave sensor based on said measured temperatures for correcting measurements performed by said microwave sensor.

40. A spinning preparation machine as in claim 39, wherein the temperature of said fiber sliver is measured continuously.

41. A spinning preparation machine as in claim 39, wherein said compensation unit is an evaluation unit of said microwave sensor.

42. A spinning preparation machine as in claim 39, wherein said compensation unit is a control unit of said spinning preparation machine.

43. A spinning preparation machine as in claim 39, including a first microwave sensor and a first temperature apparatus located before said input of said drafting equipment and a second microwave sensor and a second temperature apparatus located after said output of said drafting equipment, whereby said compensation unit receives measured results from said first and second microwave sensors and said first and second temperature apparatuses located before and after said drafting equipment and sends said measured results to a control unit to correlate such measured results.

44. A spinning preparation machine with autoleveling drafting equipment for drafting at least one fiber sliver, said spinning preparation machine including:

a multiple microwave sensors, each having a resonator through which said fiber sliver passes to measure fiber sliver thickness, at least one of said microwave sensors carried within said spinning preparation machine proximal to an input of said drafting equipment and at least one of said microwave sensors carried within said spinning preparation machine proximal to an output of said drafting equipment;

an evaluation unit in communication with said microwave sensors, said evaluation unit receiving a first measured fiber sliver thickness from said microwave sensor proximal to said input of said drafting equipment and a second measured actual sliver thickness from said microwave sensor proximal to said output of said drafting equipment with said first and said second measured actual fiber sliver thicknesses capable of being correlated by said evaluation unit; and a control unit in communication with said drafting equipment and said evaluation unit, said control unit capable of receiving information, including result of said correlations of said first and said second measured actual fiber sliver thicknesses from said evaluation unit and actuating said draft equipment so that said drafted fiber sliver obtains a target fiber sliver thickness based on said information.

45. A spinning preparation machine with autoleveling drafting equipment for drafting at least one fiber sliver, said spinning preparation machine including:

a microwave sensor having a resonator through which said fiber sliver passes to measure fiber sliver thickness, said microwave sensor carried within said spinning preparation machine proximal to at least one of an input of said drafting equipment and an output of said drafting equipment;

an evaluation unit connected and in communication with said microwave sensor, said evaluation unit receiving measured fiber sliver thickness from said microwave sensor; and a control unit connected in communication with said drafting equipment and said evaluation unit, said control unit receiving information from said evaluation unit and actuating said draft equipment so that said drafted fiber sliver obtains a target fiber sliver thickness; and wherein said microwave sensor is calibratable on the basis of calibration curves for at least one of different fiber sliver materials or fiber sliver mixtures.

46. A spinning preparation machine as in claim 45, wherein said calibration curves are storable on at least one of said evaluation unit or said control unit.

47. A spinning preparation machine as in claim 45, wherein said calibration curves are storable on an external media from which said calibration curves can be called.

48. A spinning preparation machine as in claim 45, wherein each different said fiber sliver material has at least one calibration curve provided.

49. A spinning preparation machine as in claim 48, wherein a new calibration curve is determinable based on predetermined mixture ratios of said fiber sliver mixtures.

50. A spinning preparation machine as in claim 49, wherein said new calibration is determinable by at least one of taking a mean, interpolation, and regression of at least two calibration curves.

51. A spinning preparation machine as in claim 49, further including an input unit connected in communication with said evaluation unit for the input of said mixture ratios, whereby said calibration curve is determinable by said evaluation unit from said entered mixture ratios.

52. A process for the calibration of a microwave sensor used within a spinning preparation machine for measuring fiber sliver thickness of a fiber sliver, the process including the steps of:

taking laboratory measurements of samples of at least one of the fiber sliver and fiber sliver material, which form the fiber sliver;

calculating a calibration based on the laboratory measurements; and inputting the calibration into the microwave sensor.

53. A process as in claim 52, wherein at least one skein of the fiber sliver with defined moisture content is used for calibration.

54. A process as in claim 52, wherein the fiber sliver is stored under uniform environmental condition and a sample of this fiber sliver is used for calibration.

55. A process as in claim 52, further including pouring out the samples of the fiber sliver material and hardening the material.

56. A process as in claim 52, further including taking samples of material with the same permittivity as the fiber sliver material.

57. A spinning preparation machine for drafting at least one fiber sliver, said spinning preparation machine comprising;

drafting equipment for drafting said at least one fiber sliver, said drafting equipment having a preliminary drafting field and a main drafting field;

a microwave sensor disposed within at least one of said preliminary drafting field or said main drafting field of said drafting equipment, said microwave sensor measuring fiber sliver thickness as said fiber sliver passes through said microwave sensor; and a control unit in communication with said drafting equipment and said microwave sensor, said control unit controlling the drafting equipment and capable of receiving information, including measurements of fiber sliver thickness from said microwave sensor to affect autoleveling of the fiber sliver thickness.

58. A spinning preparation machine for drafting at least one fiber sliver, said spinning preparation machine comprising;

drafting equipment for drafting said at least one fiber sliver, said drafting equipment including an input roller pair at the beginning of a preliminary drafting field;

a microwave sensor disposed before said input roller pair, said input roller pair conveying said sliver through said microwave sensor with the distance between the sensor and the input roller pair being shorter than a median staple length of the fiber sliver material being drafted; and a control unit in communication with said drafting equipment and said microwave sensor, said control unit controlling the drafting equipment and capable of receiving information, including measurements of fiber sliver thickness from said microwave sensor to affect autoleveling of the fiber sliver thickness.

* * * * *